(12) United States Patent
Rowe, III et al.

(10) Patent No.: US 8,321,283 B2
(45) Date of Patent: Nov. 27, 2012

(54) SYSTEMS AND METHODS FOR ALERTING PHARMACIES OF FORMULARY ALTERNATIVES

(75) Inventors: James C. Rowe, III, Sugar Hill, GA (US); Warren K. Williams, Atlanta, GA (US)

(73) Assignee: Per-Se Technologies, Atlanta, GA (US)

( * ) Notice: Subject to any disclaimer, the term of this patent is extended or adjusted under 35 U.S.C. 154(b) by 1246 days.

(21) Appl. No.: 11/441,554

(22) Filed: May 26, 2006

(65) Prior Publication Data
US 2006/0271402 A1 Nov. 30, 2006

Related U.S. Application Data

(60) Provisional application No. 60/685,722, filed on May 27, 2005.

(51) Int. Cl.
*G06Q 10/00* (2006.01)
(52) U.S. Cl. .................... 705/20; 705/2; 705/3
(58) Field of Classification Search .............. 705/20
See application file for complete search history.

(56) References Cited

U.S. PATENT DOCUMENTS

| | | | |
|---|---|---|---|
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,235,702 A | 8/1993 | Miller | |
| 5,237,620 A | 8/1993 | Deaton et al. | |
| 5,301,105 A | 4/1994 | Cummings | |
| 5,305,196 A | 4/1994 | Deaton et al. | |
| 5,327,508 A | 7/1994 | Deaton et al. | |
| 5,359,509 A | 10/1994 | Little et al. | |
| 5,388,165 A | 2/1995 | Deaton et al. | |
| 5,430,644 A | 7/1995 | Deaton et al. | |
| 5,448,471 A | 9/1995 | Deaton et al. | |

(Continued)

FOREIGN PATENT DOCUMENTS
CA 2482370 A1 3/2006
(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Hiep V Nguyen
(74) *Attorney, Agent, or Firm* — Sutherland Asbill & Brennan LLP (57) ABSTRACT

Methods, systems and computer program products alert pharmacies of formulary alternatives. A claim generated by a provider and including at least one drug is received, where the claim is directed to a payer recipient. The claim is reviewed to identify the at least one drug. The at least one drug is then compared to a pre-established formulary alternative table, which may be created or managed, at least in part, by the payer recipient. A preferred drug alternative may then be forwarded to the provider when the at least one drug has a match in the pre-established formulary alternative table.

20 Claims, 4 Drawing Sheets

U.S. PATENT DOCUMENTS

| | | | |
|---|---|---|---|
| 5,544,044 A | 8/1996 | Leatherman | |
| 5,550,734 A | 8/1996 | Tarter et al. | |
| 5,588,649 A | 12/1996 | Blumberg et al. | |
| 5,592,560 A | 1/1997 | Deaton et al. | |
| 5,612,868 A | 3/1997 | Off et al. | |
| 5,621,812 A | 4/1997 | Deaton et al. | |
| 5,628,530 A | 5/1997 | Thornton | |
| 5,638,457 A | 6/1997 | Deaton et al. | |
| 5,642,485 A | 6/1997 | Deaton et al. | |
| 5,644,723 A | 7/1997 | Deaton et al. | |
| 5,644,778 A | 7/1997 | Burks et al. | |
| 5,649,114 A | 7/1997 | Deaton et al. | |
| 5,659,469 A | 8/1997 | Deaton et al. | |
| 5,675,662 A | 10/1997 | Deaton et al. | |
| 5,687,322 A | 11/1997 | Deaton et al. | |
| 5,704,044 A | 12/1997 | Tarter et al. | |
| 5,748,907 A | 5/1998 | Crane | |
| 5,749,907 A | 5/1998 | Mann | |
| 5,832,447 A | 11/1998 | Rieker et al. | |
| 5,832,457 A | 11/1998 | O'Brien | |
| 5,845,255 A * | 12/1998 | Mayaud | 705/3 |
| 5,857,175 A | 1/1999 | Day et al. | |
| 5,892,827 A | 4/1999 | Beach et al. | |
| 5,892,900 A | 4/1999 | Ginter et al. | |
| 5,915,007 A | 6/1999 | Klapka | |
| 5,926,795 A | 7/1999 | Williams | |
| 5,950,169 A | 9/1999 | Borghesi et al. | |
| 5,956,736 A | 9/1999 | Hanson et al. | |
| 5,963,915 A | 10/1999 | Kirsch | |
| 5,970,469 A | 10/1999 | Scroggie et al. | |
| 5,974,399 A | 10/1999 | Giuliani et al. | |
| 5,991,750 A | 11/1999 | Watson | |
| 6,000,828 A | 12/1999 | Leet | |
| 6,006,242 A | 12/1999 | Poole et al. | |
| 6,012,035 A | 1/2000 | Freeman, Jr. et al. | |
| 6,014,634 A | 1/2000 | Scroggie et al. | |
| 6,021,392 A | 2/2000 | Lester et al. | |
| 6,026,370 A | 2/2000 | Jermyn | |
| 6,041,309 A | 3/2000 | Laor | |
| 6,055,573 A | 4/2000 | Gardenswartz et al. | |
| 6,067,069 A | 5/2000 | Krause | |
| 6,067,524 A | 5/2000 | Byerly et al. | |
| 6,073,104 A | 6/2000 | Field | |
| 6,185,541 B1 | 2/2001 | Scroggie et al. | |
| 6,195,612 B1 | 2/2001 | Pack-Harris | |
| 6,202,923 B1 | 3/2001 | Boyer et al. | |
| 6,205,455 B1 | 3/2001 | Umen | |
| 6,208,973 B1 | 3/2001 | Boyer et al. | |
| 6,224,387 B1 | 5/2001 | Jones | |
| 6,240,394 B1 | 5/2001 | Uecker | |
| 6,260,758 B1 | 7/2001 | Blumberg | |
| 6,278,979 B1 | 8/2001 | Williams | |
| 6,282,516 B1 | 8/2001 | Giuliani | |
| 6,298,330 B1 | 10/2001 | Gardenswartz et al. | |
| 6,304,849 B1 | 10/2001 | Uecker et al. | |
| 6,307,940 B1 | 10/2001 | Yamamoto et al. | |
| 6,307,958 B1 | 10/2001 | Deaton et al. | |
| 6,321,210 B1 | 11/2001 | O'Brien et al. | |
| 6,324,516 B1 | 11/2001 | Shults et al. | |
| 6,330,546 B1 | 12/2001 | Gopinathan et al. | |
| 6,334,108 B1 | 12/2001 | Deaton et al. | |
| 6,341,265 B1 | 1/2002 | Provost et al. | |
| 6,343,271 B1 | 1/2002 | Peterson et al. | |
| 6,351,735 B1 | 2/2002 | Deaton et al. | |
| 6,377,935 B1 | 4/2002 | Deaton et al. | |
| 6,424,949 B1 | 7/2002 | Deaton et al. | |
| 6,427,020 B1 | 7/2002 | Rhoads | |
| 6,484,146 B2 | 11/2002 | Day et al. | |
| 6,542,902 B2 * | 4/2003 | Dulong et al. | 707/104.1 |
| 6,584,448 B1 | 6/2003 | Laor | |
| 6,632,251 B1 | 10/2003 | Rutten et al. | |
| 6,671,692 B1 | 12/2003 | Marpe et al. | |
| 6,671,693 B1 | 12/2003 | Marpe et al. | |
| 6,684,195 B1 | 1/2004 | Deaton et al. | |
| 6,714,918 B2 | 3/2004 | Hillmer et al. | |
| 6,757,898 B1 | 6/2004 | Ilsen et al. | |
| 6,769,228 B1 | 8/2004 | Mahar | |
| 6,795,809 B2 | 9/2004 | O'Brien et al. | |
| 6,879,959 B1 | 4/2005 | Chapman et al. | |
| 6,885,994 B1 | 4/2005 | Scroggie et al. | |
| 7,013,284 B2 | 3/2006 | Guyan et al. | |
| 7,024,374 B1 | 4/2006 | Day et al. | |
| 7,058,584 B2 | 6/2006 | Kosinski et al. | |
| 7,058,591 B2 | 6/2006 | Giuliani et al. | |
| 7,111,173 B1 | 9/2006 | Scheidt | |
| 7,155,397 B2 | 12/2006 | Alexander et al. | |
| 7,225,052 B2 | 5/2007 | Foote et al. | |
| 7,228,285 B2 | 6/2007 | Hull et al. | |
| 7,233,913 B2 | 6/2007 | Scroggie et al. | |
| 7,309,001 B2 | 12/2007 | Banfield et al. | |
| 7,356,460 B1 | 4/2008 | Kennedy et al. | |
| 7,380,707 B1 | 6/2008 | Fredman | |
| 7,401,027 B2 | 7/2008 | Moore et al. | |
| 7,415,426 B2 | 8/2008 | Williams et al. | |
| 7,418,400 B1 | 8/2008 | Lorenz | |
| 7,426,480 B2 | 9/2008 | Granger et al. | |
| 7,597,247 B2 | 10/2009 | Helmin et al. | |
| 8,019,619 B2 | 9/2011 | Ghouri | |
| 2001/0001014 A1 | 5/2001 | Akins, III et al. | |
| 2001/0032099 A1 | 10/2001 | Joao | |
| 2001/0037216 A1 | 11/2001 | Oscar et al. | |
| 2001/0037224 A1 | 11/2001 | Eldridge et al. | |
| 2001/0041993 A1 | 11/2001 | Campbell | |
| 2002/0002495 A1 | 1/2002 | Ullman | |
| 2002/0035488 A1 | 3/2002 | Aquila et al. | |
| 2002/0044043 A1 | 4/2002 | Chaco et al. | |
| 2002/0049617 A1 | 4/2002 | Lencki et al. | |
| 2002/0055856 A1 | 5/2002 | Adams | |
| 2002/0065687 A1 | 5/2002 | Onoue | |
| 2002/0087554 A1 | 7/2002 | Seelinger | |
| 2002/0087583 A1 | 7/2002 | Morgan et al. | |
| 2002/0111832 A1 * | 8/2002 | Judge | 705/3 |
| 2002/0120473 A1 | 8/2002 | Wiggins | |
| 2002/0128883 A1 | 9/2002 | Harris | |
| 2002/0133503 A1 | 9/2002 | Amar et al. | |
| 2002/0138593 A1 | 9/2002 | Novak et al. | |
| 2002/0175370 A1 | 11/2002 | Bockelman | |
| 2002/0183979 A1 | 12/2002 | Wildman | |
| 2002/0198831 A1 | 12/2002 | Patricelli et al. | |
| 2003/0009357 A1 | 1/2003 | Pish | |
| 2003/0009367 A1 | 1/2003 | Morrison | |
| 2003/0028404 A1 | 2/2003 | Herron et al. | |
| 2003/0050799 A1 | 3/2003 | Jay et al. | |
| 2003/0074218 A1 | 4/2003 | Liff et al. | |
| 2003/0074222 A1 | 4/2003 | Rosow et al. | |
| 2003/0083903 A1 | 5/2003 | Myers | |
| 2003/0120588 A1 | 6/2003 | Dodd et al. | |
| 2003/0125986 A1 | 7/2003 | Collosi | |
| 2003/0149594 A1 | 8/2003 | Beazley et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0006490 A1 | 1/2004 | Gingrich et al. | |
| 2004/0019464 A1 | 1/2004 | Martucci et al. | |
| 2004/0039599 A1 | 2/2004 | Fralic | |
| 2004/0046020 A1 | 3/2004 | Andreasson et al. | |
| 2004/0049422 A1 | 3/2004 | Mortimer | |
| 2004/0054657 A1 | 3/2004 | Takeyama | |
| 2004/0073457 A1 | 4/2004 | Kalies | |
| 2004/0078234 A1 | 4/2004 | Tallal | |
| 2004/0093242 A1 | 5/2004 | Cadigan et al. | |
| 2004/0107117 A1 | 6/2004 | Denny | |
| 2004/0111277 A1 | 6/2004 | Pearson et al. | |
| 2004/0111291 A1 | 6/2004 | Dust et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0172281 A1 | 9/2004 | Stanners | |
| 2004/0188998 A1 | 9/2004 | Henthorn | |
| 2004/0249745 A1 | 12/2004 | Baaren | |
| 2005/0015280 A1 | 1/2005 | Gabel et al. | |
| 2005/0033604 A1 | 2/2005 | Hogan | |
| 2005/0033610 A1 | 2/2005 | Cunningham | |
| 2005/0060201 A1 | 3/2005 | Connely, III et al. | |
| 2005/0065821 A1 | 3/2005 | Kalies | |
| 2005/0086081 A1 | 4/2005 | Brock-Fisher | |
| 2005/0090425 A1 | 4/2005 | Reardan et al. | |

| | | | |
|---|---|---|---|
| 2005/0102169 | A1 | 5/2005 | Wilson |
| 2005/0125292 | A1 | 6/2005 | Kassab et al. |
| 2005/0154627 | A1 | 7/2005 | Zuzek et al. |
| 2005/0171815 | A1 | 8/2005 | Vanderveen |
| 2005/0187793 | A1 | 8/2005 | Myles |
| 2005/0197862 | A1 | 9/2005 | Paterson et al. |
| 2005/0240473 | A1 | 10/2005 | Ayers et al. |
| 2005/0288972 | A1 | 12/2005 | Marvin et al. |
| 2006/0015518 | A1 | 1/2006 | Eletreby et al. |
| 2006/0020514 | A1 | 1/2006 | Yered |
| 2006/0026041 | A1 | 2/2006 | Ullman |
| 2006/0085230 | A1 | 4/2006 | Brill et al. |
| 2006/0149587 | A1* | 7/2006 | Hill et al. ............................ 705/2 |
| 2006/0149784 | A1 | 7/2006 | Tholl et al. |
| 2006/0184391 | A1 | 8/2006 | Barre et al. |
| 2006/0224415 | A1 | 10/2006 | Hudson et al. |
| 2006/0229915 | A1 | 10/2006 | Kosinski et al. |
| 2006/0247948 | A1 | 11/2006 | Ellis et al. |
| 2006/0259363 | A1 | 11/2006 | Jhetam et al. |
| 2006/0271398 | A1 | 11/2006 | Belcastro |
| 2006/0271402 | A1 | 11/2006 | Rowe, III et al. |
| 2006/0271405 | A1 | 11/2006 | Cipolle et al. |
| 2006/0287886 | A1 | 12/2006 | Kitazawa |
| 2007/0005402 | A1 | 1/2007 | Kennedy et al. |
| 2007/0050209 | A1 | 3/2007 | Yered |
| 2007/0088576 | A1 | 4/2007 | de Beus et al. |
| 2007/0124177 | A1 | 5/2007 | Engleson et al. |
| 2007/0136100 | A1 | 6/2007 | Daugherty et al. |
| 2007/0179957 | A1 | 8/2007 | Gibson et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |
| 2008/0313103 | A1 | 12/2008 | Burns et al. |
| 2009/0222289 | A1 | 9/2009 | Helmus et al. |
| 2009/0313039 | A1 | 12/2009 | Cedergreen |
| 2010/0180223 | A1 | 7/2010 | Speier |

FOREIGN PATENT DOCUMENTS

| | | | |
|---|---|---|---|
| EP | 1310895 | A2 | 11/2002 |
| WO | 9106917 | A1 | 5/1991 |
| WO | 9725682 | A1 | 7/1991 |
| WO | 9503569 | A3 | 2/1995 |
| WO | 9850871 | A1 | 11/1998 |
| WO | 0039737 | A1 | 7/2000 |
| WO | 2007025295 | A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005. URL: http://www.awarix.com.

Non-Final Office Action for U.S. Appl. No. 11/608,068 mailed Jan. 11, 2010.

Non-Final Office Action for U.S. Appl. No. 11/608,068 mailed Apr. 12, 2012.

Final Office Action for U.S. Appl. No. 12/713,945 mailed May 2, 2012.

Final Office Action for U.S. Appl. No. 12/696,717 mailed May 30, 2012.

Final Office Action for U.S. Appl. No. 12/714,003 mailed Jun. 12, 2012.

Non-Final Office Action for U.S. Appl. No. 13/435,255 mailed Jul. 2, 2012.

Non-Final Office Action for U.S. Appl. No. 12/713,945 mailed Dec. 20, 2011.

Non-Final Office Action for U.S. Appl. No. 12/696,717 mailed Jan. 6, 2012.

Non-Final Office Action for U.S. Appl. No. 12/714,003 mailed Jan. 20, 2012.

Final Office Action for U.S. Appl. No. 11/608,068 mailed May 10, 2010.

Non-Final Office Action for U.S. Appl. No. 13/435,245 mailed Jul. 19, 2012.

Advisory Action for U.S. Appl. No. 121713,945 mailed Sep. 4, 2012.

Final Office Action for U.S. Appl. No. 12/714,003 mailed Sep. 12, 2012.

Final Office Action for U.S. Appl. No. 13/435,245 mailed Sep. 24, 2012.

Wermes, Mark K. "Knowing claims switches can simplify your life." Drug Store News. p. 70. Nov. 23, 1992.

Final Office Action for U.S. Appl. No. 11/608,068 mailed Aug. 2, 2012.

Non-Final Office Action for U.S. Appl. No. 13/435,241 mailed Aug. 3, 2012.

\* cited by examiner

SYSTEMS AND METHODS FOR ALERTING PHARMACIES OF FORMULARY ALTERNATIVES

RELATED APPLICATION DATA

The present application claims priority to U.S. Provisional Patent Application Ser. No. 60/685,722 filed on May 27, 2005, titled "Systems and Methods for Alerting Pharmacies of Formulary Alternatives" the entire contents of which are incorporated herein by reference as if set forth fully herein.

FIELD OF THE INVENTION

The present invention relates generally to pharmacy claim processing, and more particularly, to systems, methods and computer program products for identifying and altering pharmacies of formulary alternatives.

BACKGROUND OF THE INVENTION

The management of formulary information and processes at a retail pharmacy is a time consuming activity that diminishes overall profitability and impacts customer service. This is an expanding business issue as pharmacy claims processors expand the use of 3-tier copays and migration of patient's to higher out-of-pocket liabilities. Additionally, healthcare payers are seeking to offset rising prescription costs. Their approach is multi-fold: use higher copays to push an increasing portion of the financial liability to the patient and influence subsequent patient purchasing decisions; use formularies to influence prescribing and dispensing activities with the goal of driving the decision to a preferred product; and leverage the cost (i.e. purchasing and technology) advantages of "Mail Order" by migrating maintenance medications away from retail.

Figure 1:
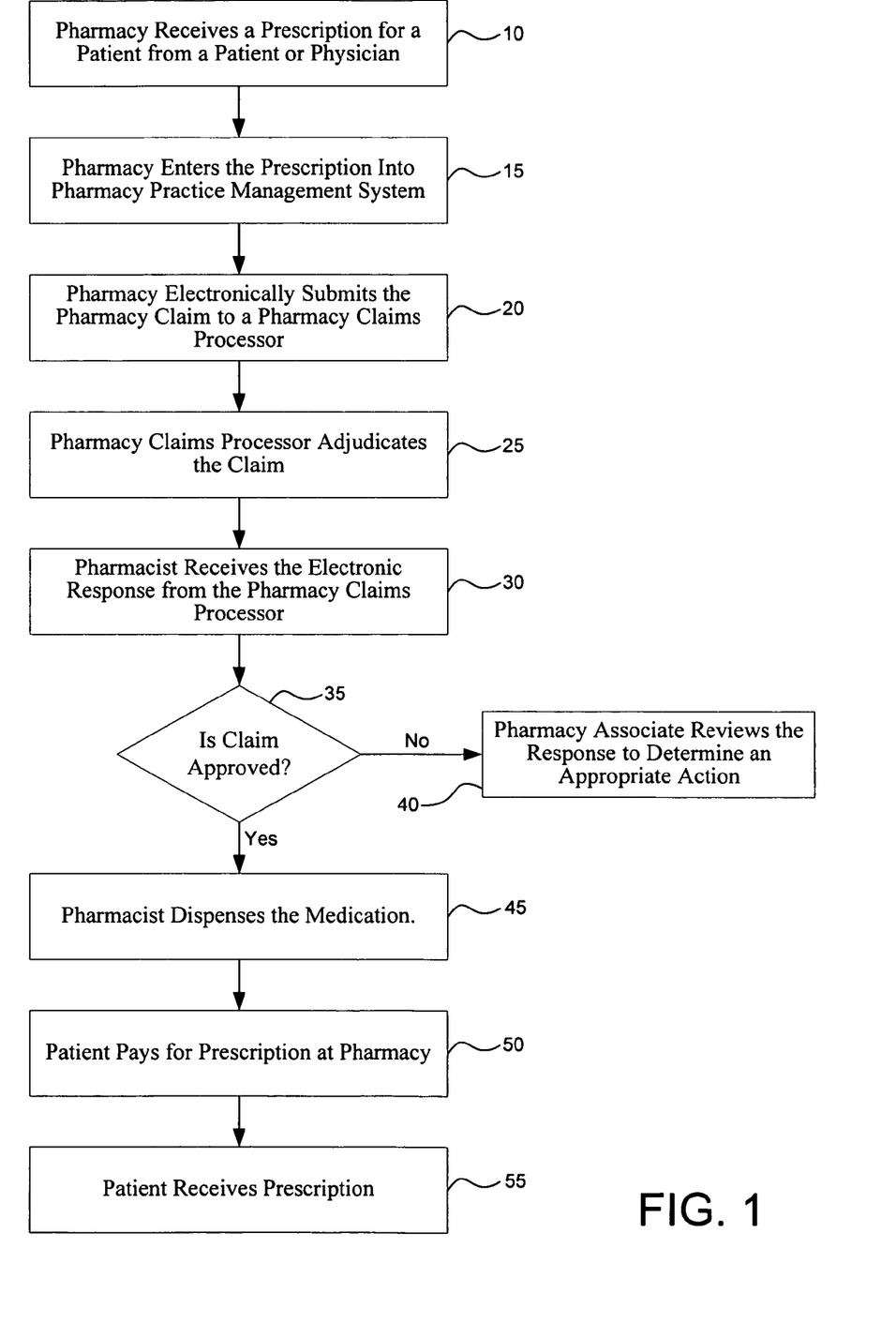
FIG. 1 shows a flow chart of a typical process by which retail pharmacies submit pharmacy claims to payers and dispense drugs to patients, according to the prior art.

FIG. 1 shows a flow chart of a typical process by which retail pharmacies submit pharmacy claims to payers and dispense drugs to patients. A pharmacy will be in receipt of a prescription for a patient after the patient or the patient's physician presents the prescription to the retail pharmacy (block 10). The pharmacy will then enter the prescription into a pharmacy practice management system or the like, which document the physician's medication therapy intent for the patient (block 15). The pharmacy will then electronically submit the claim to a pharmacy claims processor, for instance, using the pharmacy practice management system (block 20).

The pharmacy claims processor will adjudicate the claim and generate an electronic response to the pharmacy (block 25). The pharmacist (or another person associated with the pharmacy) will receive the electronic response from the pharmacy claims processor (block 30). If the claim is approved, the pharmacist begins dispensing the drugs (block 45). On the other hand, if the claim is rejected, the pharmacist reviews the response to determine an appropriate action to take (block 40). After the drugs (or medication) is dispensed, the patient pays for the prescription at the pharmacy, which may be a payment for only a partial amount of the total cost of the prescription where insurance or another provider pays for part of the prescription (block 50). The patient then receives the prescription (block 55).

The above-described process is flawed for a variety of reasons including, but not limited to the following reasons. First, at block 15, the pharmacy does not know if a formulary exists or the specifics of the formulary (e.g. preferred vs. non-preferred, patient liability, etc.) before the claim is submitted to the pharmacy claims processor (at block 20). Not knowing the formulary, the pharmacist does not have a chance to influence the dispensing decision with the physician or with the patient. When a pharmacy claim is approved (block 35), the claim response may include a message indicating an alternative product should be considered to reduce the patient's out of pocket spend. However, many pharmacists do not read or interpret free-text message fields of a claim response when a claim is approved by the pharmacy claims processor. Subsequently, the pharmacy associate may be asked by the patient or physician to identify the preferred product when the patient's financial liability is deemed too high. The present invention presents specific formulary information to the pharmacy associate prior to submitting a claim to a pharmacy claims processor.

Additionally, as described at blocks 35 and 40, if a pharmacy claim is rejected, a pharmacist is forced to review the free-from text field associated with the claim response message. Typically, most pharmacy claims processors do not reject a pharmacy claim. Instead, most claims are approved and the patient's out-of-pocket liability used to motivate the patient to switch to a preferred medication within the therapeutic category. Moreover, only after a patient arrives at a pharmacy to pick up their prescription (block 55) do patients typically refute the purchase of the prescription if their out-of-pocket expense is for a higher tier copay. This scenario creates several issues. First, the pharmacist may not have sufficient information to identify the preferred brand drug for the patient or prescriber. Second, the pharmacist has to contact the physician to authorize a different medication if the preferred drug is not a generic for the prescribed drug. Third, the pharmacist has to dispense a replacement prescription if an alternative medication is available and authorized. All of these activities affect pharmacy associate productivity and therefore overall profitability.

SUMMARY OF THE INVENTION

Systems, methods and computer program products according to the present invention generate, in response to a claim received from a pharmacy, an actionable formulary message identifying a formulary alternative, e.g., a drug alternative. The present invention may identify such alternatives when a payer, such as an insurance company refuses to pay for a prescribed drug and when prescription alternatives are available. Among other advantages, the present invention increases profitability of pharmacies by capturing incentives, improves pharmacy associate productivity, increases customer loyalty by providing optimal service, and enhances a pharmacy's ability to move market share.

According to an embodiment of the invention, the present invention identifies formulary opportunities for contracted participants (e.g., pharmacies) as a claim traverses an intermediary's network. The present invention also creates and delivers an actionable formulary message to a participating retail pharmacy, after which the pharmacist may take action, and before the pharmacy submits a claim to a payer. Thus, the present invention facilitates the delivery of a formulary message at the point of billing a prescription and before any of the dispensing activities occurs.

These actionable formulary messages benefit the pharmacy from multiple perspectives. First, the formulary message alerts the pharmacy associate when an attempt is made to bill for a non-preferred product. Currently, pharmacies do not have a good method of knowing if a drug is preferred or not preferred. Second, when the submitted drug is non-preferred, the formulary message alerts the pharmacy associate to the preferred products. This information supports a productive discussion with the patient and with the physician's office when asking for an alternative medication. Third, the formulary message alerts occur before the prescription is dispensed (i.e. medication selected, placed in container, labeled, and placed in a waiting bin) and before the customer requests their prescription and pays for it. Formulary messages provided prior to dispensing will diminish the time consuming re-work that eventually occurs when the pharmacy dispenses a non-preferred medication. Fourth, pharmacies will be financially rewarded for their therapeutic interchange activities. The present invention increases the likelihood that payers will financially reward pharmacy participants when they successfully move a patient to a preferred medication that saves them money. Fifth, the present invention permits retail pharmacies to control the decision to support "Formulary Messaging Services" and participation at the drug level.

According to another embodiment of the invention, the present invention may present patient/maintenance drug specific messages to a pharmacy to identify when a 90 day supply is appropriate for the pharmacy to dispense. According to an aspect of the invention, a formulary module may use data such as a submitted Group Number, Cardholder ID Number, Product/Service ID, and Days Supply to determine if there is an opportunity to fill the prescription with a Dispense Quantity and Days Supply that is similar to a mail-order prescription.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention is described below with reference to block diagrams and flowchart illustrations of systems, methods, apparatuses and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Exemplary embodiments of the present invention will hereinafter be described with reference to the figures, in which like numerals indicate like elements throughout the several drawings.

Figure 2:
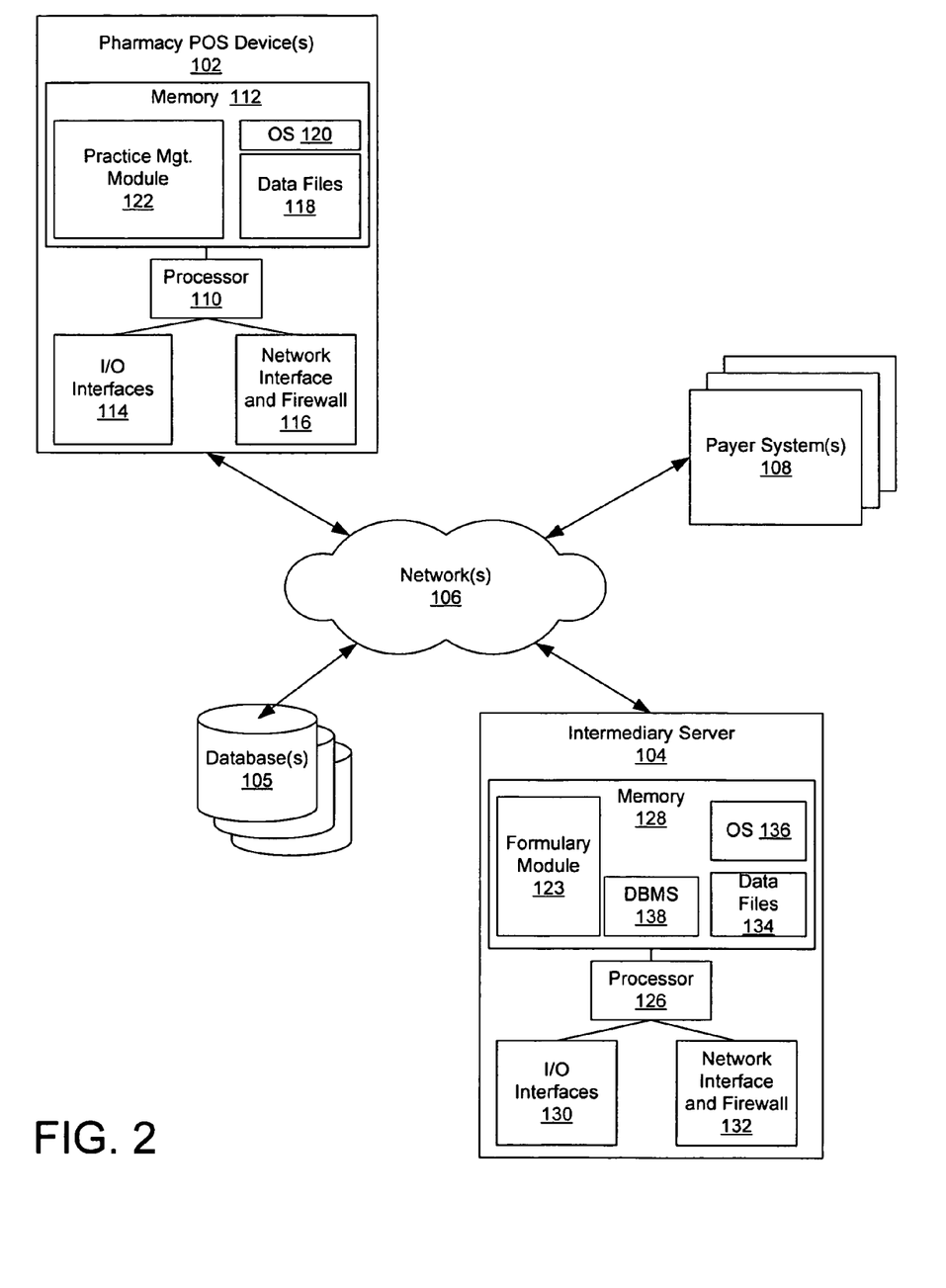
FIG. 2 shows a formulary messaging system according to an illustrative embodiment of the invention.

FIG. 2 shows a block diagram formulary messaging system according to one aspect of the present invention. In particular, FIG. 2 is an exemplary operating environment for implementation of certain embodiments of the present invention, including a pharmacy point-of-service ("POS") device 102, a intermediary server 104 and a payer system 108, which are each configured for accessing and reading associated computer-readable media having stored thereon data and/or computer-executable instructions for implementing the various methods of the present invention. Generally, network devices and systems include hardware and/or software for transmitting and receiving data and/or computer-executable instructions over a communications link and a memory for storing data and/or computer-executable instructions. Network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 2, a pharmacy POS device 102 may be in communication with the intermediary server 104 via a network 106. The pharmacy POS device 102 may be configured for receiving prescription claim data, creating prescription transactions therefrom and transmitting said prescription transactions to the intermediary server 104. Prescription claim data includes any data that is typically provided by a patient, pharmacist and/or other health care provider in relation to filling a prescription and/or requesting approval or authorization for payment from a payer or claim adjudicator.

A payer may be an insurance company, a financial institution or another financial service provider. Prescription claim data may be input to the pharmacy POS device 102 by a pharmacist or other health care provider or may be received by the pharmacy POS device 102 in electronic form from an electronic prescription service (not shown). The pharmacy POS device 102 may be configured for handling other types of prescription transactions.

Prescription claim transactions are electronic records or messages intended to facilitate the communication of prescription information. For example, prescription claim transactions are intended to communicate prescription claim data between pharmacies (i.e., providers) and payers. Although prescription claim transactions will be discussed hereinafter, it should be understood that the various systems and method of the invention may be practiced in connection with other types of prescription transactions or independently of prescription transactions (e.g., raw prescription data). The content and format of a prescription claim may vary depending on which standard or protocol is used. In general, however, prescription claim transactions will identify at least the intended payer recipient, the drug product to be dispensed, e.g., by National Drug Code number ("NDC#"), the quantity to be dispensed and the days supply, whether the prescription claim relates to a new prescription or a refill prescription, and billing-related information.

Prescription claim transactions may be transmitted from a pharmacy POS device 102 to the intermediary server 104 in batch, real-time or near real-time. Pharmacy POS device(s) 102 can connect to the intermediary server 104 through a variety of methods, including dial-up, frame relay or leased-line. The entire system is preferably supported by redundant software, communications links, and uninterruptible power supplies, thereby ensuring that all connections will provide reliable, continuous operation. The system also preferably ensures that all of provider-submitted claims transactions are routed quickly, accurately, and consistently. The claim processing system eliminates provider postage and handling expenses by allowing pharmacies (or other healthcare entities) to submit claims to payer systems 108 electronically, thereby substantially reducing the costs of submitting claims and speeding up providers' payment cycles.

In certain embodiments, the intermediary server 104 may serve as a clearinghouse for multiple payer systems 108. As noted above, payer systems 108 may include systems operated by insurance companies, financial institutions and other financial service providers. In its capacity as a clearinghouse, the intermediary server 104 is operable to parse prescription claim transactions and forward them to the appropriate payer system 108 for processing. Approval, authorization or rejection messages may be returned to the intermediary server 104 from the payer systems 108 and such messages may be forwarded by the intermediary server 104 to the pharmacy POS device 102.

In serving as a clearinghouse, the intermediary server 104 may also be configured for performing pre-processing and post-processing of prescription claim transactions. Pre-processing and post-processing refers to real-time or near real-time validation and management of prescription claim data in order to maximize prescription claim reimbursement and minimize claim submission errors. Pre-processing and post-processing may generate messaging alerts and/or retrospective reports supporting "usual and customary" price comparisons, average wholesale price ("AWP") edits, dispense as written ("DAW") brand appropriateness, and numerous other screening processes for facilitating rapid and accurate validation of prescription claims.

In accordance with the present invention, the intermediary server 104, and more particularly, the formulary module 123, may be configured for performing certain formulary screening processes to create an actionable formulary message transmitted to the pharmacy POS device(s) 102. This message includes an identification of when a pharmacy attempts to bill for a non-preferred product. The formulary message may include patient-specific formulary messages when there is an opportunity to reduce the patient's out of pocket financial liability, along with the payer's financial liability. For instance, the present invention may alert a pharmacy if a payer will not fully reimburse its client for a particular drug when a generic alternative is available.

According to an aspect of the invention, the formulary message alerts occur before the prescription is dispensed (i.e. medication selected, placed in container, labeled, and placed in a waiting bin) and before the customer requests their prescription and pays for it. Formulary messages provided prior to dispensing will diminish the time consuming re-work that eventually occurs when the pharmacy dispenses a non-preferred medication. Therefore, it will be appreciated that the formulary module 123 may comprise computer-executable instructions for performing various formulary screening processes for reviewing pharmacy claims and for managing related messaging and reporting functions.

According to an embodiment of the present invention, the intermediary server 104 receives a claim transmitted from the pharmacy POS device 102, and the formulary module 123 parses and examines the claim's contents. According to another embodiment of the invention, the formulary module 123 is located external to the intermediary server 104. According to an embodiment of the invention, the intermediary server 104 may represent, or be part of, an intermediary network, which receives claims from the pharmacy POS device(s) 102. After identifying that claims include an actionable formulary item, the intermediary server 104 (or the intermediary network) may forward the claim to the external formulary module 123, which is in communication with the intermediary network or server 104.

After the formulary module 123 identifies that there is a formulary opportunity, and returns a rejected response to the pharmacy POS device 102 with a formulary message. The pharmacy may then decide if it is going to respond to the alert or if is going to bypass the alert. If the pharmacy responds to the alert, the pharmacy contacts the prescriber if the preferred drug is a therapeutic alternative and chemically unique. Upon receipt of the new prescription, the pharmacy re-submits the claim to the intermediary server 104. Thereafter, the pharmacy receives reimbursement for the claim along with a financial incentive.

Referring again to FIG. 2, it will be appreciated that the pharmacy POS device 102 may be any processor-driven device, such as a personal computer, laptop computer, hand-held computer and the like. In addition to a processor 110, the pharmacy POS device 102 may further include a memory 112, input/output ("I/O") interface(s) 114 and a network interface 116. The memory 112 may store data files 118 and various program modules, such as an operating system ("OS") 120 and a practice management module 122. The practice management module 122 may comprise computer-executable instructions for performing various routines, such as those for creating and submitting prescription claim transactions. I/O interface(s) 114 facilitate communication between the processor 110 and various I/O devices, such as a keyboard, mouse, printer, microphone, speaker, monitor, etc. The network interface 116 may take any of a number of forms, such as a network interface card, a modem, etc. These and other components of the pharmacy POS device 102 will be apparent to those of ordinary skill in the art and are therefore not discussed in more detail herein.

Similarly, the intermediary server 104 may be any processor-driven device that is configured for receiving and fulfilling requests related to prescription claim transactions. The intermediary server 104 may therefore include a processor 126, a memory 128, input/output ("I/O") interface(s) 130 and a network interface 132. The memory 128 may store data files 134 and various program modules, such as an operating system ("OS") 136, a database management system ("DBMS") 138 and the formulary module 123. The intermediary server 104 may include additional program modules (not shown) for performing other pre-processing or post-processing methods and for providing clearinghouse services. Those skilled in the art will appreciate that the intermediary server 104 may include alternate and/or additional components, hardware or software. In addition, the intermediary server 104 may be connected to a local or wide area network (not shown) that includes other devices, such as routers, firewalls, gateways, etc.

The intermediary server 104 may include or be in communication with one or more database(s) 105. The database 105 may store, for example, formulary information, data relating to pharmacies, payers, state prescription laws, prescription drugs, and consumers, such as typical doses filled by consumers, typical drugs prescribed by doctors, most common daily dose values, common daily dose values, likelihood indicators and other data used in the various claim screening and editing processes described herein after. The database 105 may also store reports and other data relating to the results of the claim screening and edit processes. The database 105 may of course also store any other data used or generated by the intermediary server 104 or formulary module 123, such as data used in other pre-processing and post-processing methods and reports generated thereby. Although a single database 105 is referred to herein for simplicity, those skilled in the art will appreciate that multiple physical and/or logical databases may be used to store the above mentioned data. For security, the intermediary server 104 may have a dedicated connection to the database 105. However, the intermediary server 104 may also communicate with the database 105 via a network 106, as shown.

The network 106 may comprise any telecommunication and/or data network, whether public or private, such as a local area network, a wide area network, an intranet, an internet and/or any combination thereof and may be wired and/or wireless. Due to network connectivity, various methodologies as described herein may be practiced in the context of distributed computing environments. Although the exemplary pharmacy POS device 102 is shown for simplicity as being in communication with the intermediary server 104 via one intervening network 106, it is to be understood that any other network configuration is possible. For example, the pharmacy POS device 102 may be connected to a pharmacy's local or wide area network, which may include other devices, such as gateways and routers, for interfacing with another public or private network 106. Instead of or in addition to a network 106, dedicated communication links may be used to connect the various devices of the present invention.

Those skilled in the art will appreciate that the operating environment shown in and described with respect to FIG. 2 is provided by way of example only. Numerous other operating environments, system architectures and device configurations are possible. For example, the invention may in certain embodiments be implemented in a non-networked environment, in which a stand-alone pharmacy POS device 102 executes one or more claim editing module(s) 123. Accordingly, the present invention should not be construed as being limited to any particular operating environment, system architecture or device configuration.

Using the formulary processing system described above, pharmacies can transmit claims in real-time or near real-time and receive formulary messages to alert pharmacies when an attempt is made to bill for a non-preferred product. To enable the pharmacy to input claims for electronic transmission to the claim processing system and payer, the pharmacy POS device 102 may comprise software that receives claim data entered by a user through a graphical user interface (GUI). According to one aspect of the invention, no claim processing software resides on the POS device 102, other than an Internet browser, because the GUI and one or more interfaces for inputting claim data are stored by the claim processing system and remotely accessible by the POS device 102 via an Internet connection, satellite or cellular network, LAN, WAN, or the like.

Using the GUI information such as a patient's name, birth date, address, telephone number and other identifying information is entered with claim-specific information, such as drug prescription or medical service or procedure. The identity of the pharmacy is also included in the claim data along with additional information known to those of ordinary skill in the art.

According to one aspect of the invention the claim data fields are defined by a particular payer such that the POS device 102 should provide only the claim data requested by the payer to which the claim is transmitted. According to another aspect of the invention the claim data is defined by a pre-established standard or transaction format well known to those of skill in the art. Once the claim is entered, it is transmitted to the intermediary server 104 via any of the methods described above. The claim is then processed by the intermediary server 104 and forwarded to the appropriate payer system 108. Preferably, the claim processing system, and more particularly, the intermediary server 104, is an all-payer solution allowing providers to use a single application to connect to key government and commercial payers across the country.

The present invention will next be described with respect to several embodiments which may utilize the systems described in detail above. It will be appreciated that these embodiments are illustrative and non-limiting examples, and are not intended as the only embodiments of the present invention.

A. Payer Formularies on a Network

According to one embodiment of the invention, payer formularies are managed by the intermediary server 104. Thus, although the database(s) 105 are illustrated as separate from the intermediary server 104, they may be controlled, managed and/or located within the intermediary server 104.

Figure 3:
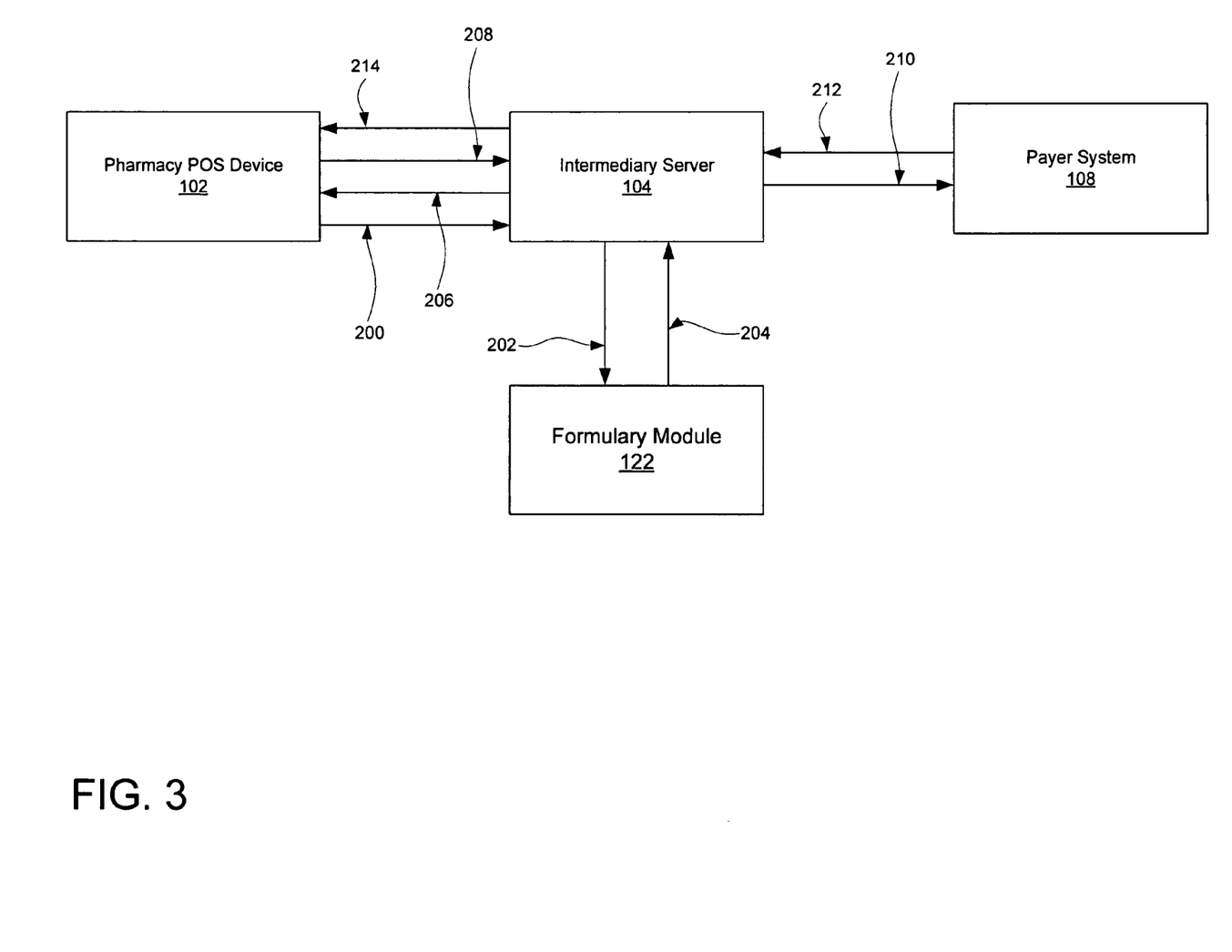
FIG. 3 shows communications in a formulary messaging system, according to an illustrative embodiment of the invention.

Referring now to FIG. 3, in this embodiment, a pharmacy may submit a claim transaction (200) to the intermediary server 104. The intermediary server 104, recognizes the transaction includes a formulary messaging services opportunity. This may occur when the intermediary server 104 parses the claim and identifies that one or more fields identify that a prescribed drug is part of the claim received from a pharmacy. The intermediary server 104 then forwards (202) the transaction to the formulary module 123. According to an aspect of the invention, the formulary module 123 identifies a formulary message opportunity and generates a rejected response (204) for transmission (206) by the intermediary server 104 to the pharmacy POS device(s) 102. The pharmacy, can respond to the opportunity by changing the originally prescribed drug to a preferred formulary medication.

Next, the pharmacy re-submits (208) the claim transaction to the intermediary server 104. Once again, by parsing the claim the intermediary server 104 recognizes that the transaction includes a formulary messaging services opportunity. The intermediary server 104 forwards the transaction to the formulary module 123, which recognizes that the transaction is not a formulary messaging opportunity, as the prescribed drug is a preferred drug. As a result, the formulary module 123 forwards (210) the transaction to the payer system(s) 108. The payer system(s) 108 adjudicates the claim request, and returns a response (212) to the intermediary server 104, which in turn returns the response (214) to the pharmacy POS device 102. As described above, it will be appreciated that the intermediary server 104 may be an intermediary network 104, and that the formulary module 123 is local or remote from the intermediary network. Thus, according to an aspect of the invention, the intermediary network may handle all communications with the pharmacy POS device 102 and the payer system 108, such that the formulary module 123 only communicates with the intermediary network.

B. Formulary Inquiry Transactions to Payer

Figure 4:
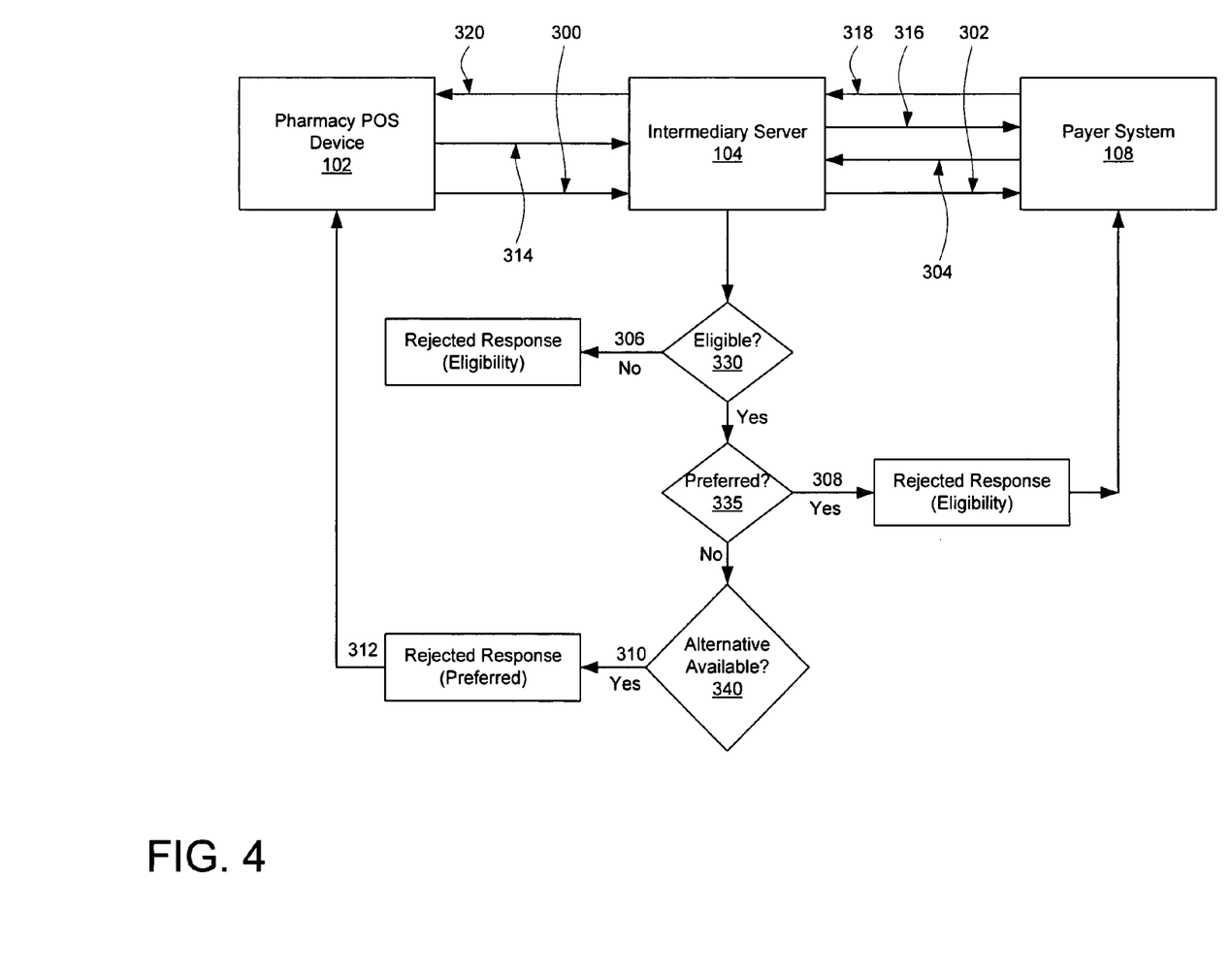
FIG. 4 shows communication in a formulary messaging system, according to an illustrative embodiment of the invention.

According another embodiment of the invention, the intermediary server 104 may include a combination of editing and transaction processing capabilities. For certain pharmacies and payers, the intermediary server 104 may recognize if a submitted claim is for a specified "Payer Group". In general, if a positive match occurs, the intermediary server 104 can format a formulary inquiry transaction for transmission to the pharmacy claims processor. The pharmacy claims processor responds to the inquiry, after which the intermediary server 104 determines if the response from the pharmacy POS device 102 is positive. If "Positive", the intermediary server 104 formats a rejected response to the pharmacy POS device 102. If "Negative", the intermediary server 104 forwards the claim inquiry to the payer system 108.

Such an embodiment will be described in more detail with reference to the process flow of FIG. 4. First, a pharmacy POS device 102 submits (300) a claim transaction into the intermediary server 104. The intermediary server 104 recognizes that the transaction is for a formulary messaging services opportunity. As described above, this may occur when the intermediary server 104 parses the claim and identifies that one or more fields identify that a prescribed drug is part of the claim received from a pharmacy. Other method known to those of ordinary skill in the art may be used. The intermediary server 104 then creates an "Eligibility/Formulary Inquiry" transaction from the claim request, and holds the "Claim Request". Thereafter, the intermediary server 104 submits (302) the "Eligibility/Formulary Inquiry" transaction to the payer system 108. The payer system 108 accepts and processes the "Eligibility/Formulary Inquiry" transaction and determines, based on an examination of the patient's account, whether: the patient is eligible (Yes/No), the medication submitted is preferred (or not preferred), if there are alternative medications identified (including the name of preferred medications), and/or the alternative medications/patient pay amounts per submitted quantity. The payer system 108 then returns an eligibility response (304) to the intermediary server 104. The intermediary server 104, upon receipt of the eligibility response and parses the response to determine if the patient is eligible (330). If not (306), the intermediary server 104 creates and return the eligibility denial back to the pharmacy POS device 102 as a rejected response. If eligible (330), the intermediary server 104 examines the eligibility response to determine if the submitted medication is a preferred medication (335). If so (308), the intermediary server 104 immediately submits the prescription as a "Claim Request" to the payer system 108.

If the medication is not preferred, and an alternative medication(s) exists (340), the intermediary server 104 creates and returns a rejected claim response (312) to the pharmacy with the alternative medications and calculated copays present in the response. The rejected claim response may include formulary information in one or more message fields. The pharmacy POS device 102 can respond to the opportunity by changing the originally prescribed drug to a preferred formulary medication, and re-submits (314) the claim transaction to the intermediary server 104. The intermediary server again recognizes that the transaction is for a formulary messaging services" opportunity, and recognizes that the transaction is follow-up claim to an initial formulary inquiry. The intermediary server 104 then forwards (316) the claim request to the payer system 108. The payer system 108 adjudicates the claim request and returns a response (318) to the intermediary server 104, after which the intermediary server 104 may return the response to the pharmacy POS device 102.

C. Patient/Maintenance Drug Specific Messages

According to yet another illustrative embodiment of the invention, the present invention may present patient/maintenance drug specific messages to a pharmacy to identify when a 90 day supply is appropriate for the pharmacy to dispense. According to an aspect of the invention, a formulary module may use information including Group Number, Cardholder ID Number, Product/Service ID, and/or Days Supply to determine if there is an opportunity to fill the prescription with a dispense quantity and days supply that is similar to a mail-order prescription.

According to an illustrative example, a pharmacy may submit a prescription claim to the intermediary server. The intermediary server 104 may recognizes that there is a "Mail Order" opportunity for the submitted drug, e.g., by comparing the drug identified in the claim to a table listing mail order opportunities. The intermediary server 104 may then return a rejected response to the claim with a "Mail Order" message. The pharmacy may then decide if it is going to respond to the message or bypass the message, which typically requires a user's input. If the pharmacy responds to the message, the pharmacy contacts the prescriber when the prescription "Dispense Quantity" and "Refills Authorized" does not support a "Maintenance Drug" dispensing. Upon receipt of the new prescription, the pharmacy re-submits the pharmacy claim. The pharmacy then receives reimbursement for the claim. This method and service may be advantageous to payers determined to control their drug spend by migrating their patient population group to preferred products within a therapeutic category, and supporting reimbursement for prescriptions at mail-order rates.

D. Formulary Module Identification of Actionable Formulary Opportunities

It will be appreciated by those of ordinary skill in the art that the formulary module 123 may determine whether a formulary opportunity is actionable by using a lookup table that correlates prescribed drugs to alternatives. The formulary module 123 may also use user or drug-specific tables that use characteristics of a prescribed drug, or other factors, such as the age of the patient, to identify formulary suggestions. These tables may also be controlled in part or in whole by the payer system 108, such that the payer can dictate what drugs the intermediary server and formulary module 123 should take action on.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of alerting pharmacies of formulary alternatives, comprising:
receiving, by at least one computer processor of an intermediary server in communication with a pharmacy and a payer recipient, a claim generated by the pharmacy from a pharmacy practice management system, wherein the claim comprises at least one drug, wherein the claim is directed to the payer recipient, and wherein the claim is received by the payer recipient prior to forwarding by the intermediary server any formulary alternatives to the at least one drug;
reviewing, by at least one computer processor, the claim to identify the at least one drug as a drug the payer recipient has preselected;
comparing, by at least one computer processor, the at least one drug to a pre-established formulary alternative table established, at least in part, by the payer recipient, wherein the pre-established formulary alternative table comprises one or more preferred drug alternatives based at least in part on cost differences between the at least one drug and the one or more preferred drug alternatives; and
forwarding a preferred drug alternative to the pharmacy practice management system when the at least one drug has a match in the pre-established formulary alternative table, wherein the preferred drug alternative is forwarded via an alert that can be responded to or bypassed by the pharmacy practice management system.

2. The method of claim 1, wherein the pharmacy practice management system comprises a pharmacy processor-driven device, personal computer, laptop computer, or handheld computer.

3. The method of claim 1, wherein the claim identifies a patient associated with the payer recipient.

4. The method of claim 1, wherein forwarding a preferred drug alternative to the pharmacy comprises forwarding the preferred drug alternative to the pharmacy via an alert that may be accepted or declined by the pharmacy.

5. The method of claim 1, further comprising receiving a new claim from the pharmacy for the preferred drug alternative.

6. The method of claim 5, further comprising forwarding the new claim to the payer recipient.

7. The method of claim 6, further comprising: receiving a response from the payer recipient subsequent to the payer recipient's adjudication of the new claim; and instructing the pharmacy that the new claim is approved.

8. The method of claim 1, wherein the pre-established formulary alternative table comprises formulary information or drug-specific tables.

9. The method of claim 1, wherein the claim comprises content defined by the payer recipient.

10. A system of alerting pharmacies of formulary alternatives, comprising:
an intermediary server, in communication with a provider, wherein the intermediary server is operable to:
receive a claim generated by a pharmacy from a pharmacy practice management system, where the claim is directed to a payer recipient, and where the claim comprises at least one drug preselected by the payer recipient, wherein the claim is received by the payer recipient prior to forwarding by the intermediary server any formulary alternatives to the at least one drug;
review the claim to identify the at least one drug; compare the at least one drug to a pre-established formulary alternative table established, at least in part, by the payer recipient, wherein the pre-established formulary alternative table comprises one or more preferred drug alternatives based at least in part on cost differences between the at least one drug and the one or more preferred drug alternatives; and
forward a preferred drug alternative to the pharmacy practice management system when the at least one drug has a match in the pre-established formulary alternative table, wherein the preferred drug alternative is forwarded to the pharmacy practice management system via an alert that may be accepted or declined by the pharmacy practice management system.

11. The system of claim 10, wherein the pharmacy practice management system comprises a pharmacy point of sale (POS) device.

12. The system of claim 10, wherein the claim identifies a patient associated with the payer recipient.

13. The system of claim 10, wherein the intermediary server is local to the pharmacy.

14. The system of claim 10, wherein the intermediary server is in communication with the pharmacy via at least one network.

15. The system of claim 10, wherein the intermediary server is further operable to forwarding the preferred drug alternative to the pharmacy practice management system via an alert that may be accepted or declined by the pharmacy practice management system.

16. The system of claim 10, wherein intermediary server is further operable to receive a new claim from the pharmacy practice management system for the preferred drug alternative.

17. The system of claim 16, wherein the intermediary server is further operable to transmit the new claim to the payer recipient.

18. The system of claim 17, wherein the intermediary server is further operable to: receive a response from the payer recipient subsequent to the payer recipient's adjudication of the new claim; and instruct the pharmacy that the new claim is approved.

19. The system of claim 10, wherein the pre-established formulary alternative table comprises formulary information or drug-specific tables.

20. The system of claim 10, wherein the claim comprises content defined by the payer recipient.

* * * * *